US00PP23561P2

(12) United States Plant Patent
Smith

(10) Patent No.: US PP23,561 P2
(45) Date of Patent: Apr. 23, 2013

(54) ***CHRYSANTHEMUM* PLANT NAMED 'SYMILD YEL'**

(50) Latin Name: *Chrysanthemum×morifolium*
Varietal Denomination: Symild Yel

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 256 days.

(21) Appl. No.: 13/065,982

(22) Filed: Apr. 4, 2011

(51) Int. Cl.
*A01H 5/00* (2006.01)

(52) U.S. Cl. ..... Plt./289

(58) Field of Classification Search ..... Plt./289
See application file for complete search history.

*Primary Examiner* — Annette Para
(74) *Attorney, Agent, or Firm* — Joshua L. Price

(57) ABSTRACT

A new *Chrysanthemum* plant named 'Symild Yel' particularly distinguished by the large, yellow inflorescences, medium green foliage, good mounded plant habit and a natural flowering season response of about mid October.

1 Drawing Sheet

Latin name of the genus and species of the plant claimed: *Chrysanthemum×morifolium.*

Varietal denomination: 'Symild Yel'.

BACKGROUND OF THE NEW PLANT

The present invention comprises a new *Chrysanthemum*, botanically known as *Chrysanthemum×morifolium*, and hereinafter referred to by the variety name 'Symild Yel'.

'Symild Yel' is a product of a planned breeding program. The new cultivar has large, yellow inflorescences, medium green foliage, good mounded plant habit and a natural flowering season response of about mid October.

'Symild Yel' originates as a natural whole plant mutation of 'Yomildred', U.S. Plant Pat. No. 21,187. 'Symild Yel' was discovered and selected by the inventor as a single flowering plant within a population of the parent cultivar in a controlled breeding program in Alva, Fla. in December 2008. The parent cultivar 'Yomildred' has white inflorescence color, a little larger plant habit and a natural season flowering response that is a few days faster.

The first act of asexual reproduction of 'Symild Yel' was accomplished when vegetative cuttings were propagated from the initial selection in January 2008 in a controlled environment in Alva, Fla.

BRIEF SUMMARY OF INVENTION

Horticultural examination of plants grown from cuttings of the plant initiated in January 2008, and continuing thereafter, has demonstrated that the combination of characteristics as herein disclosed for 'Symild Yel' are firmly fixed and are retained through successive generations of asexual reproduction.

'Symild Yel' has not been observed under all possible environmental conditions. The phenotype may vary significantly with variations in environment such as temperature, light intensity and day length.

A Plant Breeder's Right for this cultivar was applied for in Canada on Apr. 9, 2010 (No. 10-6933). 'Symild Yel' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Symild Yel' with colors being as true as possible with an illustration of this type. The photographic drawing shows a flowering potted plant of the new variety.

DETAILED BOTANICAL DESCRIPTION

The plant used for the photographs was about 16 weeks old grown in Monroeville, N.J. in an outdoor trial. One rooted cuttings grown in a nine inch pot with no terminal pinching of the apices. The photograph was taken in mid October 2010 in New Jersey.

The plant descriptions and measurements were taken in Gilroy, Calif. in May 2010 under natural light. Plants were grown under conditions which approximate those generally used for potted *Chrysanthemum* trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYMILD YEL' AND A SIMILAR VARIETY

| | 'Symild Yel' | 'Summy Yobrigitte' (U.S. Plant Pat. No. 13,973) |
|---|---|---|
| Inflorescence size: | Little larger | Little smaller |
| Plant habit: | More mounded/less height/more width | Less mounded/more upright |

Plant:

*Form, growth, and habit.*—Herbaceous decorative garden-type, stems upright and outwardly spreading, freely branching, strong and moderately Vigorous growth habit.

*Plant height.*—10-12 cm.
*Plant height* (*inflorescence included*).—18-20 cm.
*Plant width.*—20-23 cm.
*Garden performance and tolerance to weather.*—Very good.

Roots:
*Number of days to initiate roots.*—4 days at about 22 degrees C.
*Number of days to produce a rooted cutting.*—10-12 days at 22 degrees C.
*Type.*—Fine, fibrous, free branching.
*Color.*—RHS N155B but whiter.

Foliage:
*Arrangement.*—Alternate.
*Immature, leaf color, upper surface.*—RHS 137A but a little darker.
*Lower surface.*—Closest to RHS 138B.
*Mature, leaf color, upper surface.*—RHS 137A but a little darker.
*Lower surface.*—Closest to RHS 138B.
*Length.*—6.0-6.5 cm.
*Width.*—3.8-4.5 cm.
*Shape.*—Ovate.
*Base shape.*—Attenuate.
*Apex shape.*—Acute to apiculate.
*Margin.*—Irregularly and palmately lobed; serrate.
*Texture, upper surface.*—Bifid T-shaped hairs.
*Lower surface.*—Bifid T-shaped hairs.
*Color of veins, upper surface.*—Closest to RHS 144A.
*Color of veins, lower surface.*—Closest to RHS 144A.
*Petiole color.*—Closest to RHS 144A.
*Length.*—2.2-2.9 cm.
*Diameter.*—0.2 cm.
*Texture.*—Heavily Bifid T-shaped hairs.

Stem:
*Quantity of main branches per plant.*—5-6.
*Color of stem.*—RHS 146A.
*Length of stem.*—12-15 cm.
*Diameter.*—0.3-0.5 cm.
*Length of internodes.*—0.4-0.7 cm.
*Texture.*—Bifid T-shaped hairs.
*Color of peduncle.*—RHS 146A.
*Length of peduncle.*—7-10 cm.
*Peduncle diameter.*—0.2-0.25 cm.
*Texture.*—Bifid T-shaped hairs.

Inflorescence:
*Type.*—Compositae type, solitary inflorescences, decorative-type, borne terminally above foliage, ray florets arranged acropetally on a capitulum.
*Quantity of short days to flowering* (*response time*).—Approximately 55 days.
*Quantity of inflorescences per plant.*—50-55.
*Lastingness of individual blooms on the plant.*—About 6 weeks from the first color.
*Fragrance.*—Slightly spicy.

Bud (just when opening/showing color):
*Color.*—RHS 4B with RHS 4A apex.
*Length.*—0.5-0.9 cm.
*Width.*—0.5-0.6 cm.
*Shape.*—Oblate.

Immature inflorescence:
*Diameter.*—5.0-5.5 cm.
*Color of ray florets, upper surface.*—RHS 4A.
*Lower surface.*—RHS 4D.

Mature inflorescence:
*Diameter.*—7-7.5 cm.
*Depth.*—2.0-2.5 cm.
*Total diameter of 'disc'.*—0.3-0.4 cm (but not visible).
*Receptacle height.*—0.3-0.5 cm.
*Receptacle diameter.*—0.6-0.7 cm.

Ray florets:
*Average quantity of florets.*—150 in numerous whorls.
*Color of florets, upper surface.*—RHS 4B with RHS 4A apex; sometimes fading to RHS 4C.
*Lower surface.*—RHS 4D.
*Length.*—2.9-3.2 cm.
*Width.*—0.7-0.8 cm.
*Shape.*—Elliptical.
*Apex shape.*—Praemorse.
*Margin.*—Entire.
*Texture, upper surface.*—Papillose.
*Lower surface.*—Papillose.

Disc florets:
*Average quantity of florets.*—7-10.
*Color of florets.*—RHS 1C but more green with RHS 1A apex.
*Length.*—0.5-0.6 cm.
*Width.*—0.1 cm.
*Shape.*—Tubular, elongated.
*Apex shape.*—Acute, 5 pointed.

Phyllaries:
*Quantity.*—28-30.
*Color, upper surface.*—RHS 137A to RHS 137B.
*Lower surface.*—RHS 137A to RHS 137B.
*Length.*—0.8-0.9 cm.
*Width.*—0.15 cm.
*Shape.*—Lanceolate.
*Apex shape.*—Acute.
*Base.*—Fused.
*Margins.*—Entire.
*Texture, upper surface.*—Bifid T-shaped hairs.
*Lower surface.*—Bifid T-shaped hairs.

Reproductive organs:
*Pistil.*—1.
*Length.*—0.5 cm.
*Style color.*—RHS 1C.
*Style length.*—0.3-0.4 cm.
*Stigma color.*—RHS 12A.
*Stigma shape.*—Bi-parted.
*Ovary color.*—Not observed.
*Stamens.*—1.
*Color of filaments.*—RHS 1C.
*Length filaments.*—0.2-0.3 cm.
*Anther color.*—RHS 17B.
*Anther length.*—0.15 cm.
*Anther shape.*—Oval.
*Color of pollen.*—RHS 17A.
*Pollen amount.*—Some observed.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Symild Yel' substantially as illustrated and described herein.

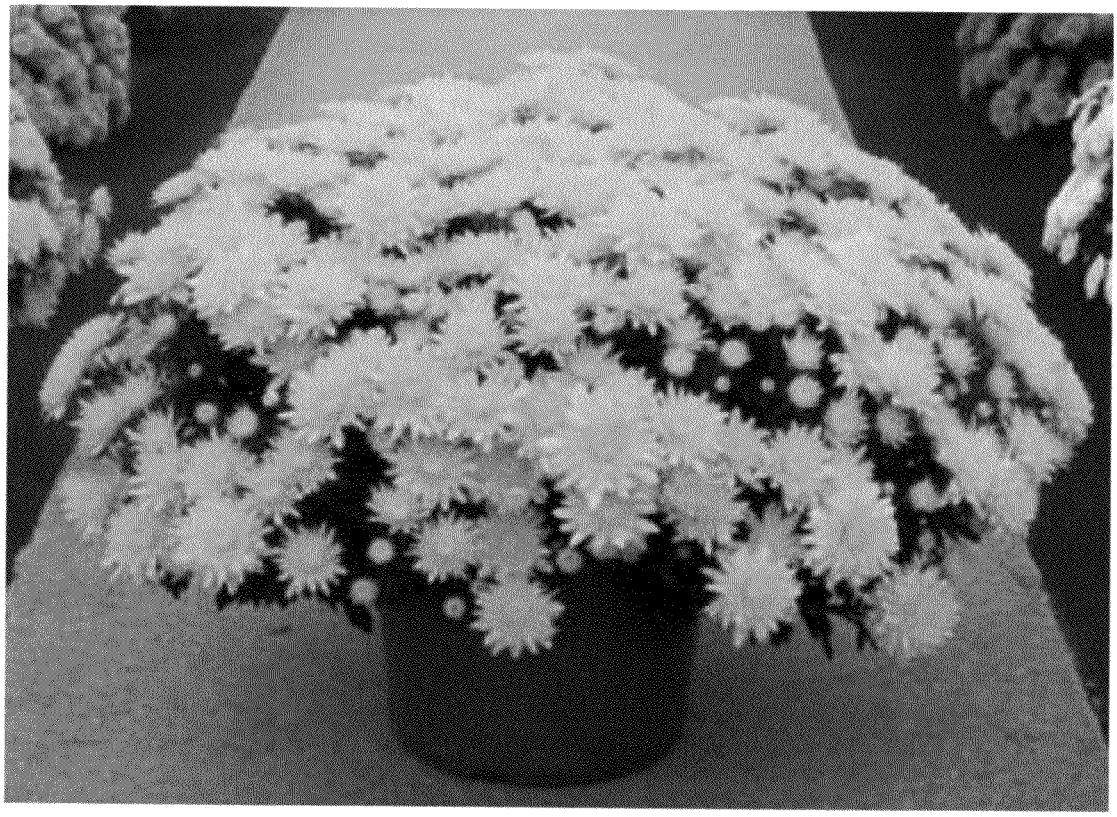

* * * * *